United States Patent
Pforr et al.

(10) Patent No.: US 6,404,841 B1
(45) Date of Patent: Jun. 11, 2002

(54) IMAGE THICKNESS SELECTION FOR MULTISLICE IMAGING SYSTEM

(75) Inventors: Carl Pforr, Milwaukee; Hui David He, Waukesha, both of WI (US); Sholom M. Ackelsberg, Ridgewood, NJ (US); Xiangfeng Ni, Milwaukee, WI (US); Chalapathy V. Dhanwada, Arlington Heights, IL (US); Carlos F. Guerra, Lake Mills, WI (US); Holly A. McDaniel, New Berlin, WI (US); Gary R. Strong, Waukesha, WI (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 0 days.

(21) Appl. No.: 09/473,676

(22) Filed: Dec. 29, 1999

Related U.S. Application Data

(60) Provisional application No. 60/114,183, filed on Dec. 30, 1998.

(51) Int. Cl.[7] .................................................. A61B 6/00
(52) U.S. Cl. .............................. 378/4; 378/19; 378/12; 378/15
(58) Field of Search ................................ 378/4, 19, 12, 378/15

(56) References Cited

U.S. PATENT DOCUMENTS

| | | | |
|---|---|---|---|
| 4,361,902 A | 11/1982 | Brandt et al. | |
| 5,469,487 A | 11/1995 | Hu | |
| 5,513,236 A | 4/1996 | Hui | |
| 5,541,970 A | 7/1996 | Hu | |
| 5,559,847 A | 9/1996 | Hu et al. | |
| 5,606,585 A | 2/1997 | Hu | |
| 5,828,719 A | 10/1998 | He et al. | |
| 6,023,494 A * | 2/2000 | Senzig et al. | 378/4 |
| 6,061,420 A * | 5/2000 | Strong et al. | 378/4 |
| 6,115,448 A | 9/2000 | Hoffman | |
| 6,198,791 B1 * | 3/2001 | He et al. | 378/19 |
| 6,275,562 B1 * | 8/2001 | He et al. | 378/19 |

FOREIGN PATENT DOCUMENTS

| | | |
|---|---|---|
| EP | 0 564 182 A2 | 6/1993 |
| WO | WO 98/05980 | 2/1998 |

* cited by examiner

Primary Examiner—David P. Porta
Assistant Examiner—Pamela R. Hobden
(74) Attorney, Agent, or Firm—Carl B. Horton, Esq.; Armstrong Teasdale, LLP

(57) ABSTRACT

Scalable multislice systems which, in one embodiment, includes a scalable multislice detector, a scalable data acquisition system (SDAS), scalable scan management, control, and image reconstruction processes, and a user interface, are described. More specifically, the user interface is implemented in a host computer for defining the configuration of the imaging system. Particularly, after selection of each scan parameter, the user interface displays the available scan parameter values for the remaining parameters so that the scan objectives are met. More specifically, after selection of each scan parameter, the user interface updates the remaining scan parameters, including prospective and retrospective image thicknesses.

17 Claims, 7 Drawing Sheets

|         | THICKNESS (mm) |
| ------- | -------------- |
| HELICAL | 1.25  2.50  3.75  5.00  7.50  10.00 |

SCAN MODE
HI-Q  HI-SPEED

SPEED (mm/rot)
3.75  7.50  11.25  15.00  22.50  30.00

|       | THICKNESS (mm) |
| ----- | -------------- |
| AXIAL | 1.25  2.50  3.75  5.00  7.50  10.00 |

NUMBER OF IMAGES PER ROTATION
1i  2i  4i

FIG. 3

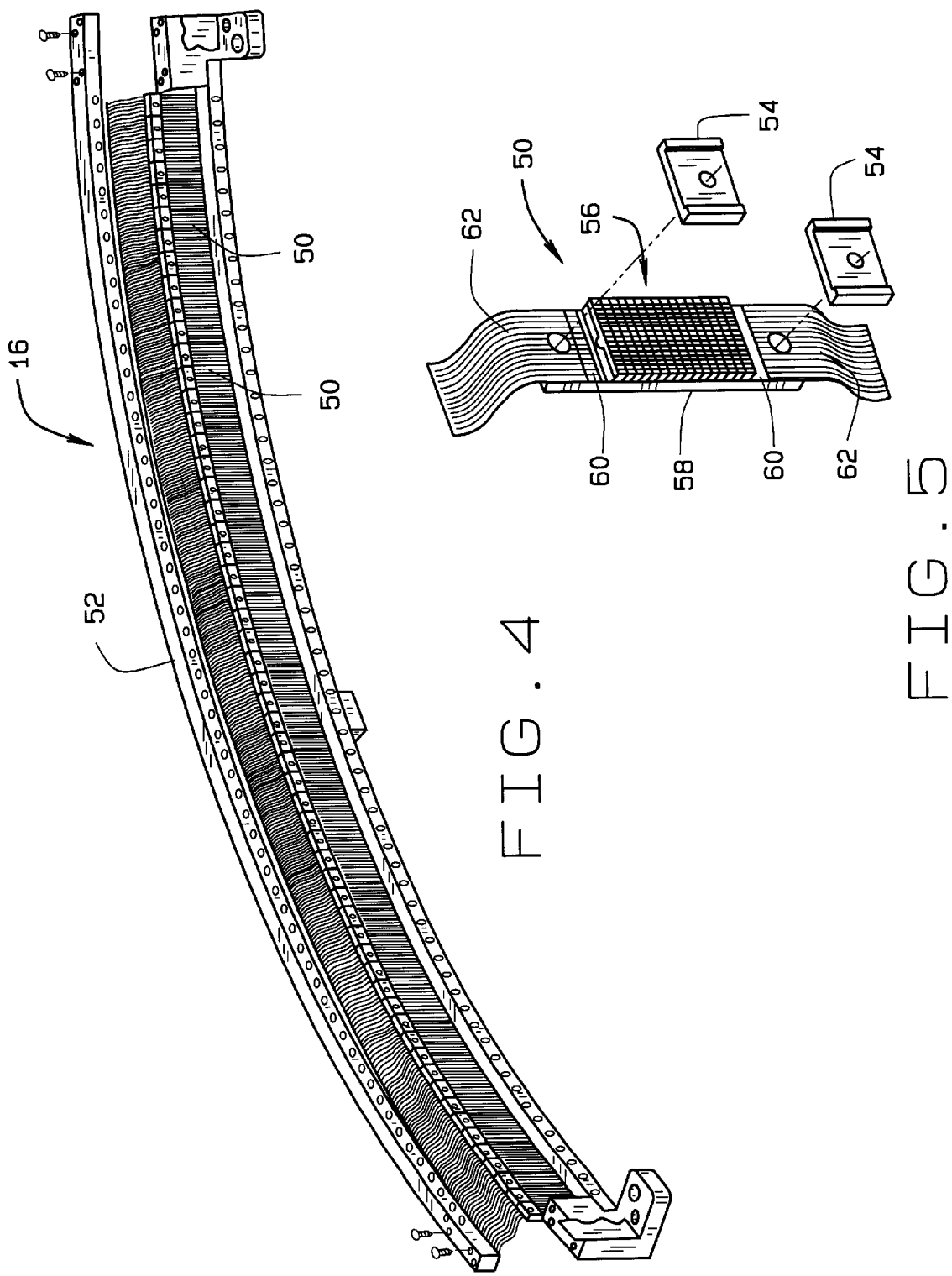

IMAGE THICKNESS SELECTION FOR MULTISLICE IMAGING SYSTEM

CROSS REFERENCE TO RELATED APPLICATIONS

This application claims the benefit of U.S. Provisional Application No. 60/114,183, filed Dec. 30, 1998.

BACKGROUND OF THE INVENTION

This invention relates generally to imaging and, more particularly, to image thickness selection for scalable multislice imaging systems.

In at least some imaging systems generally referred as computed tomography (CT) systems, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. X-ray sources typically include x-ray tubes, which emit the x-ray beam at a focal spot. X-ray detectors typically include a collimator for collimating x-ray beams received at the detector, a scintillator adjacent the collimator, and photodiodes adjacent the scintillator.

In at least one known imaging system, the transmission profile collected from the detector represents a single slice of a patient. For single slice scanning, prospective and retrospective slice thicknesses are always identical. That is, only images having the slice thickness of the collected data may be generated. Therefore, in order to generate thin slice images, thin slice data must be collected. As result, large amounts of data must be stored for each image.

It would be desirable to provide a multislice CT system that can be used to collect one, two or more slices of data. It also would be desirable to provide such a multislice CT system that provides an operator with information related to available scan parameters so that the appropriate scan prescribed may be completed. In addition, it is desirable that the remaining scan parameters be updated based on prior scan parameter selections. Additionally, it is desirable that the configuration of the multislice system be automatically adjusted for the selected scan parameters.

BRIEF SUMMARY OF THE INVENTION

In an exemplary embodiment a scalable multislice system includes a scalable multi-slice detector, a scalable data acquisition system (SDAS), scalable scan management, control, and image reconstruction processes, and scalable image user interface. As used herein, the term scalable generally means that an operator can readily and simply select the desired number of slices and the slice thickness for images to be displayed. The system enables the operator to select 1, 2, 4 or more slices to be displayed at a selected slice thickness. By enabling the system operator to make such selections, the image data for different clinical applications can be displayed in a most optimum format. No known multislice system provides an operator with such flexibility.

More specifically, and in an exemplary embodiment, the system includes a host computer coupled to a monitor for displaying images and messages to the operator. The host computer is coupled to a keyboard and a mouse to enable the operator to input information and commands to the host computer. The user interface is implemented using an instruction set stored in the host computer and enables the operator to select certain scan parameters including the desired number of slices and slice thickness. The host computer also is coupled to a scan and reconstruction control unit (SRU) which includes image generation controls.

A stationary controller is connected to the SRU, and the stationary controller is coupled to a table controller for controlling motion of the patient table. The stationary controller also is connected, through a slipring, to an on-board (i.e., on the gantry) controller and to a scalable data acquisition system (SDAS). The on-board controller controls operation of the x-ray source and operation of the SDAS, which converts analog signals from the scalable detector to digital data. The x-ray source includes a cam collimator controlled by the on-board controller. The position of the cams of the cam collimator are adjusted based on the desired number of slices and the desired slice thickness as defined by the operator using the user interface.

The system also includes a detector having a number (e.g., 57) of modules. Each module, in an exemplary embodiment, includes a scintillator array and a photodiode array. In the exemplary embodiment, the scintillator and photodiode arrays each are 16×16 arrays. The photodiodes are coupled to a switching apparatus which, in the one embodiment, includes an array of FETs, and the FETs control the combination of photodiode outputs based on the desired number of slices and slice thickness input the operator.

In operation, prior to performing a scan, the operator utilizes the user interface to prescribe certain scan parameters (e.g., a helical, axial, or cine scan, a table speed, and a pitch). After selection of each scan parameter, the options available for the remaining scan parameters are updated by the user interface. Based on the selections of the remaining scan parameters, the host computer, utilizing the user interface, presents the operator with prospective image thickness and retrospective image thickness options. Utilizing the displayed options, the operator may alter the prescribed scan parameters to achieve the desired prospective and retrospective image thicknesses. After confirming the selection, the prescribed scan parameters are used to configure system 10.

After transferring the configuration information to the appropriate elements of system 10, e.g., the detector, the SDAS, the collimator, as defined by the selected scan parameters, the prescribed scan is performed. More specifically, the photodiode outputs are supplied to the SDAS, via the FETs, for analog to digital conversion. The digital outputs from the SDAS are then supplied to the SRU via the slipring for image generation. Specifically, the SRU reconstructs images from the collected data, and such reconstructed images can be displayed to the user on the monitor or archived, or both. In addition, the operator may generate the available retrospective image thicknesses.

The above described scalable multislice system can be easily and simply operated to collect one, two, or more slices of data. Such system user interface provides the operator with available scan parameter options. In addition, the user interface updates the remaining scan parameters based on prior scan parameter selections. Additionally, the configuration of the multislice system is automatically adjusted for the selected scan parameters.

BRIEF DESCRIPTION OF THE DRAWINGS

FIG. 3 is an exemplary embodiment of a scan user interface than can be used in conjunction with the system illustrated in FIGS. 1 and 2.

FIG. 4 is a perspective view of a CT system detector array.

FIG. 5 is a perspective view of a detector module shown in FIG. 4.

DETAILED DESCRIPTION OF THE INVENTION

Figure 1:
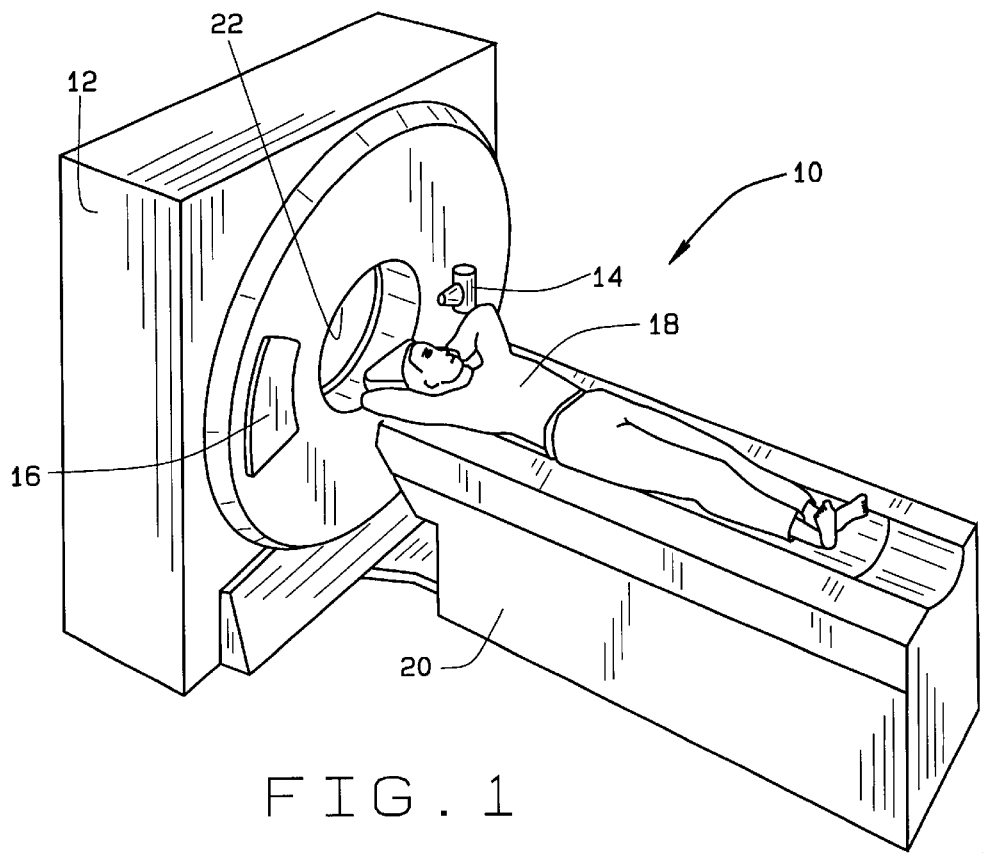
FIG. 1 is a pictorial view of a CT imaging system.

Referring to FIG. 1, a computed tomography (CT) imaging system 10 in accordance with one embodiment of the present invention is shown as including a gantry 12 representative of a "third generation" CT scanner. Gantry 12 has an x-ray source 14 that projects a beam of x-rays toward a detector array 16 on the opposite side of gantry 12. Detector array 16 is formed by a plurality of detector modules which together sense the projected x-rays that pass through a medical patient 18. Each detector module produces an electrical signal that represents the intensity of an impinging x-ray beam and hence the attenuation of the beam as it passes through patient 18.

During a scan to acquire x-ray projection data, gantry 12 and the components mounted thereon rotate about a center of rotation. A motorized table 20 positions patient 18 relative to gantry 12. Particularly, table 20 moves portions of patient 18 through a gantry opening 22 during a scan.

Figure 2:
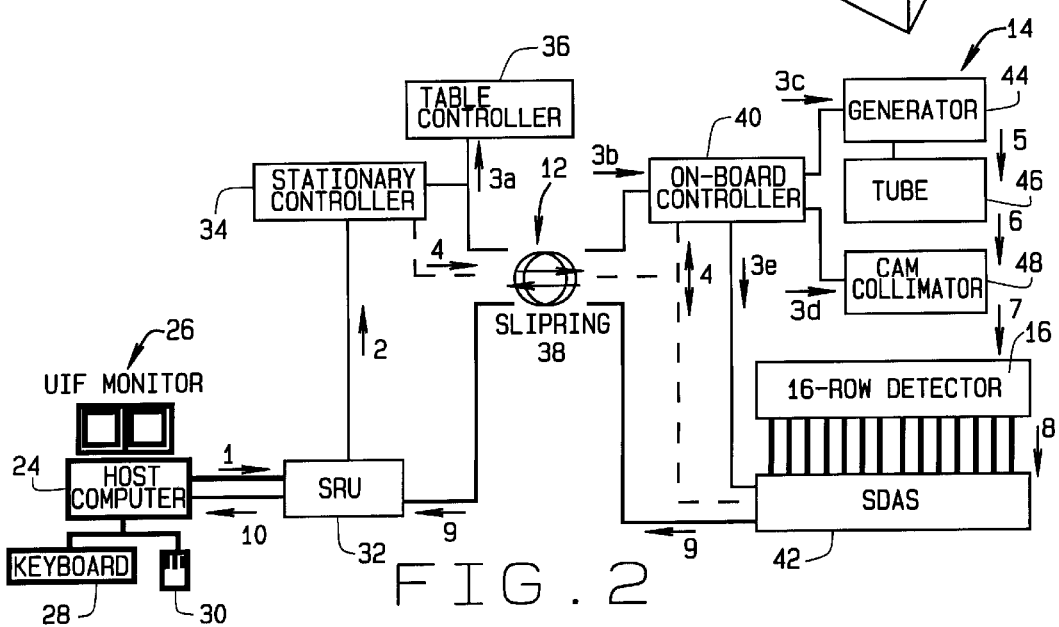
FIG. 2 is a block schematic diagram of the system illustrated in FIG. 1.

FIG. 2 is a block schematic diagram of the system illustrated in FIG. 1. As shown in FIG. 2, system 10 includes a host computer 24 coupled to a monitor 26 for displaying images and messages to an operator. Computer 24 includes a user interface (not shown) and also is coupled to a keyboard 28 and a mouse 30 to enable the operator to input information and commands to computer 24. Computer 24 is coupled to a scan and reconstruction control unit (SRU) 32. SRU 32 also includes image generation controls. In one specific embodiment, SRU 32 includes a SGI PCI-based central processing unit which operates on an IRIX operating system. SRU 32 also includes an interface processor for interfacing with the data acquisition system (described below), and a scan data correction digital signal processing board for performing preprocessing, which is known in the art. SRU 32 further includes an image generator for filtered backprojection and postprocessing operations, as is known in the art.

A stationary controller 34 is connected to SRU 32, and controller 34 is coupled to a table controller 36. Stationary controller 34 also is connected, through a slipring 38, to an on-board controller 40 and a scalable data acquisition system (SDAS) 42. Slipring 38 enables contactless transmission of signals across the slipring boundary and supports the necessary bandwidth for transmission of data and commands across the boundary. SDAS 42 samples and acquires the data from detector 16 and converts the sampled analog signals to digital signals. SDAS 42, in one specific embodiment, includes forty eight interchangeable converter cards to support four row data acquisition. For two row data acquisition, twenty four cards could be used. In one specific embodiment, there are sixty four input channels per converter card and 1408 Hz sampling can be performed. SDAS 42 also includes a front-end pre-amplifier for amplifying the signals. Further details regarding SDAS are set forth below.

On-board controller 40 controls operation of x-ray source 14 and operation of SDAS 42. X-ray source 14 includes a high voltage generator 44 coupled to an x-ray tube 46. Tube 46 may, for example, be the tube known in the art is the Gemini-1 tube and currently utilized in at least some CT system commercially available from General Electric Company, Milwaukee, Wis., 53201. Beams projected by X-ray tube 46 pass through a prepatient cam collimator 48 and impinge upon detector 16 (illustrated as a 16 row detector). Cam collimator 48 also is controlled by on-board controller 40. Outputs from detector 16 are supplied to SDAS 42.

In FIG. 2, data flow is illustrated by bold lines, control flow is illustrated by normal lines, and real-time control flow is illustrated by dotted lines. The numeric identifiers associated with the flows are set forth below.

1: scan and reconstruction prescription from operator
   2: scan prescription to "master" controller
   3: scan parameters distributed
      3a: table position
      3b: rotating parameters
      3c: kV and mA selections
      3d: x-ray beam collimation and filter selections
      3e: detector slice thickness and SDAS gain selections
   4: real-time control signals during scanning
   5: high voltage
   6: un-collimated x-ray beam
   7: collimated x-ray beam
   8: analog scan data
   9: digital scan data
   10: patient images Rotation of gantry 12 and the operation of x-ray source 14 are governed by controller 34. On-board controller 40, under the control of stationary controller 34, provides power and timing signals to x-ray source 14. SDAS 42 samples analog data from detector 16 and converts the data to digital signals for subsequent processing. SRU 32 receives sampled and digitized x-ray data from SDAS 42 and performs high speed image reconstruction. The reconstructed image is applied as an input to computer 24 which stores the image in a mass storage device.

Computer 24 also receives commands and scanning parameters from an operator via keyboard 28 and mouse 30. Monitor 26 allows the operator to observe the reconstructed image and other data from computer 24. The operator supplied commands and parameters are used by computer 24 to provide control signals and information. In addition, controller 36 controls motorized table 20 to position patient 18 (FIG. 1).

Generally, the above described CT system is operable to collect 1, 2 or more slices data. Axial, helical and cine scans can be performed with the system, and cross section images of a scanned object can be processed, reconstructed, displayed and/or archived. Scalable axial image reconstruction and display refers, for example, to selectability of the image thickness, number of slices, and number of images to be displayed. Further, the system is not limited to practice with any one particular image reconstruction algorithm, and it is contemplated that many different reconstruction algorithms can be utilized. Exemplary algorithms are set forth in U.S. Pat. Nos. 5,469,487, 5,513,236, 5,541,970, 5,559,847, and 5,606,585, and in co-pending U.S. patent application Ser. Nos. 08/561,382 (filed Nov. 21, 1995), 08/779,961 (filed Dec. 23, 1996), and 08/797,101 (filed Nov. 26, 1997), all of which are assigned to the present assignee, and all of which are incorporated herein, in their entirety, by reference.

In the axial multi-slice scan mode, multiple rows of scan data can be processed before image reconstruction, and the data can be used to produce either multiple thin slices or a reduced number of thicker slices with reduced image artifact. In addition, images with thicker slice thicknesses can be later reconstructed retrospectively into thinner slices of images based on clinical diagnosis needs. As a result, the number of unwanted images for viewing, filming, and archiving is reduced. In addition, high z-axis resolution images can be later reconstructed for patient diagnosis.

Exemplary axial multi-slice modes are set forth below in Table 1.

TABLE 1

| Acquisition Image Thickness & Mode | | Retrospective Reconstruction Image Thickness Available |
|---|---|---|
| 1.25 mm | 4i | 1.25, 2.5, 5 mm |
| 2.5 mm | 2i | 1.25, 2.5, 5 mm |
| 2.5 mm | 4i | 2.5, 5, 10 mm |
| 3.75 mm | 4i | 3.75, 7.5 mm |
| 5 mm | 1i | 1.25, 2.5, 5 mm |
| 5 mm | 2i | 2.5, 5, 10 mm |
| 5 mm | 4i | 5, 10 mm |
| 7.5 mm | 2i | 3.75, 7.5 mm |
| 10 mm | 1i | 2.5, 5, 10 mm |
| 10 mm | 2i | 5, 10 mm |

As one specific example, and for an axial mode acquisition for a 2.5 mm image thickness in the 2i mode, several retrospective reconstruction options that can be selected. For example, 4 images having a slice thickness of 1.25 mm can be reconstructed, 2 images having a slice thickness of 2.5 mm can be reconstructed, and 1 image having a slice thickness of 5 mm can be reconstructed. Accordingly, more images (e.g., 4 images) having a thinner slice thickness can be retrospectively reconstructed than the mode (i.e., 2i) in which the scan was performed. In addition, fewer images (e.g., 1 image) having a thicker slice thickness can be retrospectively reconstructed than the mode in which the scan was performed.

In the helical multi-slice scan mode, multiple combinations of patient table speed and x-ray beam and detector collimations, enable generation of images having different z-axis resolution can be produced. For example, at the table speed of 30 mm/rotation, images of 5–10 mm slices can be generated. Thicker slice (such as 10 mm) images can be generated prospectively, which provides the benefit of a reduced number of images and reduced image reconstruction time. At a later time, thinner slice images can be generated retrospectively using the same data. Such thinner slice images may be necessary depending on the clinical application needs and can be generated without rescanning the patient.

Exemplary helical multi-slice modes are set forth below in Table 2.

TABLE 2

| Table Speed (mm/rotation) | | Retrospective Reconstruction |
|---|---|---|
| Hi-Q Scan Mode | Hi-Speed Scan Mode | Image Thicknesses Available |
| 3.75 | 7.5 | 1.25, 2.5 mm |
| 7.5 | 15 | 2.5, 3.75, 5 mm |
| 11.25 | 22.5 | 3.75, 5, 7.5 mm |
| 15 | 20 | 5, 7.5, 10 mm |

For example, in a high quality image (Hi-Q) scan mode of 3.75 mm/rotation (i.e., the patient table moves 3.75 mm for each gantry rotation), or in a high speed (Hi-Speed) scan mode of 7.5 mm/rotation, images having slice thicknesses of 1.25 mm and 2.5 mm can be reconstructed retrospectively. As with the axial multi-slice mode, many other alternatives are possible depending upon the particular construction of the system components. Again, such flexibility in retrospective reconstruction provides many advantages including enabling the generation of images having the necessary resolution yet reducing the memory necessary for storing the desired images.

Further, and with respect to archiving images, the system enables storage of fewer images which require less storage space. For example, if 20 mm of patient anatomy is scanned in the 2i mode, 80 images can be generated. Storing 80 images for 20 mm of patient anatomy requires a large amount of memory. It is often the case that high resolution is not required for the entire 20 mm of patient anatomy. For example, it may be that only about 5 mm of the anatomy requires such high resolution. Using the data collected in 2.5 mm thickness 2i mode scan, the operator can retrospectively reconstruct images having a thickness of 5 mm for the majority of the anatomy, and thinner image slices (e.g., 1.25 mm) only at the locations where higher resolution is required. Using this retrospective reconstruction, the number of images to be archived can be significantly reduced.

Selection of the above described prospective and retrospective reconstruction is provided through the user interface, and possible because the scan data is collected using a multislice detector which is described below in more detail. With the thin slice scan data available, the operator, via the user interface, can select from many different slice thicknesses when performing retrospective reconstruction.

FIG. 3 is an exemplary embodiment of a user interface than can be used in conjunction with the system illustrated in FIGS. 1 and 2, for example as a graphical user interface (GUI). The interface is implemented using an instruction set stored in host computer 24 (FIG. 2) and displayed on host computer monitor 26. From the user interface, an operator selects available scan parameters to define the prescribed scan in order to define the configuration of system 10. The selections are made, for example, by the user simply touching the desired area corresponding to the desired parameters. Touch sensitive interfaces are well known.

More specifically, the user interface provides the operator with available choices, or options, for each of the scan parameters as described above. Particularly, after selection of each scan parameter, options, or choices, for each remaining scan parameter are updated in "real-time" and displayed so that the operator may select from those options available for the remaining parameters. Upon completion of the selections for the prescribed scan, the user interface displays the selected prospective image thickness and the available retrospective image thicknesses. Reviewing this information, the operator may accept the selected scan parameters or may revise one or any of the scan parameters to perform the desired scan.

More particularly, initially the operator selects a mode of operation of system 10, e.g., helical, axial or cine mode. For each selected mode, available options are displayed, using monitor 26, so that the operator may select the remaining scan parameters, e.g., image thickness, pitch, speed of table 20, and image quality. In one embodiment, after the operator has completed selection of the scan parameters, the user interface displays the prospective image thickness and the retrospective image thicknesses using different characteristics to indicate available options, or choices. Specifically, each available option, or choice, may be displayed using a first characteristic and unavailable options may be displayed on monitor 26 using a second characteristic.

For example and in one embodiment, after selecting a helical mode, available options for pitch, table speed, and image thicknesses are displayed to the user via monitor 26 for selection by the operator. After making the scan parameter selections, including the prospective image thickness, each retrospective scan parameter option available to the operator may be displayed using various colors or shades of gray. Those options which are unavailable to the operator are displayed using a second characteristic, for example so the unavailable options are visible but cannot be selected by the operator. By examining the displayed scan parameters, the operator may quickly and easily identify all of the possible options, or alternatives, for the scan parameters. Of course, many other types of interfaces could be used, and the interface illustrated in FIG. 3 is only an exemplary interface.

In one embodiment, for example, prior to performing a helical mode scan, the operator selects, from the user interface, the desired slice thickness, the scan mode, and the scan speed. The "Hi-Q" scan corresponds to a high image quality scan and the "Hi-Speed" scan corresponds to a fast patient table speed, as described above in connection with Table 2. Depending upon the selections made by the operator, various retrospective options are displayed on monitor 26. For example, a first retrospective image thickness option may be displayed in a first color and each subsequent retrospective image thickness option may be displayed in a different color, (e.g., a second color, a third color, etc.). For example, if the operator selects the scan parameters for a 5 mm and 2i scan, available retrospective image thickness options of 2.5 mm, 5 mm, and 10 mm will be displayed using a different color for each available option, e.g. 2.5 mm in red, 5 mm in blue, and 10 mm in green. In one embodiment, the unavailable image thicknesses of 1.25 mm and 3.75 mm will be visibly displayed but will be un-selectable by operator. After the operator has confirmed the selection, system 10 is configured to perform the prescribed scan.

In an axial scan, for example, the operator selects the desired slice thickness and the number of images to be generated per rotation using the user interface, For example, if the operator selects the scan parameters for a 3.75 mm 4i scan, the 3.75 mm and 7.5 mm retrospective image thickness options will displayed so that the operator may select either of these available options. The 1.25 mm, 2.5 mm, 5 mm, and 10 mm options will be visible but cannot be selected by the operator.

Before now, no multi-slice CT system provides the scalable scan management, control, and image reconstruction processes, and scalable image display and analysis, as provided with the present system.

With the present system, an operator can readily and simply select the desired number of slices and the slice thickness for images to be displayed. In addition, increased patient scan speed, improved image quality, and reduced x-ray tube loading are achieved.

Set forth below is a description of an exemplary scalable multislice CT system components in accordance with one embodiment of the present invention. The scan parameters, as defined by the operator using the user interface, are utilized to define the configuration of system 10 as detailed below. Although specific component details are set forth below, it should be understood that many alternative embodiments are possible. For example, although one particular detector SDAS and slipring are described, other embodiments of detectors, SDASs, and sliprings could be used, and the present invention is not limited to practice with any one particular type of detector, SDAS, or slipring. For example, the detector described below includes a plurality of modules and each module includes a plurality of detector cells. Rather than the specific detector described below, a detector which has non-segmented cells along the z-axis, and/or a detector which has multiple modules with multiple elements along the x-axis and/or z-axis can be joined together in either direction to acquire scalable multislice scan data simultaneously, can be utilized.

With respect to one specific detector configuration, and referring to FIGS. 4 and 5, detector 16 includes a plurality of detector modules 50. Each detector module 50 is secured to a detector housing 52 by plates 54. Each module 50 includes a multidimensional scintillator array 56 and a high density semiconductor array (not visible). A post patient collimator (not shown) is positioned over and adjacent scintillator array 56 to collimate x-ray beams before such beams impinge upon scintillator array 56. Scintillator array 56 includes a plurality of scintillation elements arranged in array, and the semiconductor array includes a plurality of photodiodes arranged in an identical array. The photodiodes are deposited, or formed on a substrate 58, and scintillator array 56 is positioned over and secured to substrate 58.

Switch and decoder apparatus 60 are coupled to the photodiode array. The photodiodes are optically coupled to scintillator array 56 and have electrical output lines for transmitting signals representative of the light output by scintillator array 56. Particularly, each photodiode produces a separate low level analog output signal that is a measurement of the beam attenuation for a specific scintillator of scintillator array 56. The photodiode output lines extend from opposing sides of the semiconductor, or photodiode, array and are connected (e.g., wire bonded) to respective apparatus 60.

Switch apparatus 60 is a multidimensional semiconductor switch array of similar size as the photodiode array, and switch apparatus 60 is coupled in electric circuit between the semiconductor array and SDAS 42 (FIG. 2). Apparatus 60, in one embodiment, includes a plurality of field effect transistors (FETs) arranged as a multidimensional array. Each FET includes an input line electrically connected to one of the respective photodiode output lines, an output line, and a control line (not shown). FET output and control lines are electrically connected to SDAS 42 via a flexible electrical cable 62. Particularly, about one-half of photodiode output lines are electrically connected to each FET input line one side of the array with the other one-half of photodiode output lines electrically connected to the FET input lines on the other side of the array.

The decoder controls the operation of the FETs to enable, disable, or combine photodiode outputs in accordance with a desired number of slices and slice resolutions for each slice. The decoder, in one embodiment, is a decoder chip or a FET controller as known in the art, and the decoder includes a plurality of output and control lines coupled to the FETs and SDAS 42. Particularly, the decoder outputs are electrically connected to the switch apparatus control lines to enable the FETs to transmit the proper data. The decoder control lines are electrically connected to the FET control lines and determine which of the outputs will be enabled. Utilizing the decoder, specific FETs are enabled, disabled, or have their outputs combined so that specific photodiode outputs are electrically connected to SDAS 42. Further details regarding detector 16 are set forth in co-pending U.S. patent application Ser. No. (15-CT-4631), Photodiode Array For A Scalable Multislice Scanning Computed Tomography System, which is assigned to the present assignee and hereby incorporated herein, in its entirety, by reference.

In one specific embodiment, detector 16 includes fifty-seven detector modules 50. The semiconductor array and scintillator array 56 each have an array size of 16×16. As a result, detector 16 has 16 rows and 912 columns (16×57 modules), which enables 16 simultaneous slices of data to be collected with each rotation of gantry 12. Of course, the present invention is not limited to any specific array size, and it is contemplated that the array can be larger or smaller depending upon the specific operator needs. Also, detector 16 may be operated in many different slice thickness and number modes, e.g., one, two, and four slice modes. For example, the FETs can be configured in the four slice mode so that data is collected for four slices from one or more rows of the photodiode array. Depending upon the specific configuration of the FETs as defined by decoder control lines, various combinations of photodiode outputs can be enabled, disabled, or combined so that the slice thickness may, for example, be 1.25 mm, 2.5 mm, 3.75 mm, or 5 mm. Additional examples include, a single slice mode including one slice with slices ranging from 1.25 mm thick to 20 mm thick, and a two slice mode including two slices with slices ranging from 1.25 mm thick to 10 mm thick. Of course, many other modes are possible.

Figure 6:
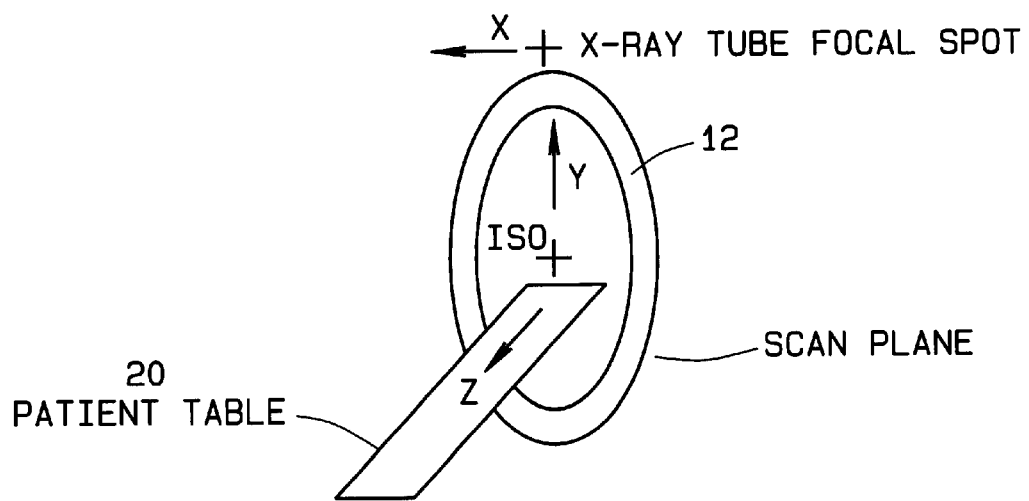
FIG. 6 illustrates the geometric configuration of the CT system illustrated in FIG. 1.

FIG. 6 illustrates the geometric configuration of the CT system illustrated in FIG. 1 and shows the gantry coordinate system. The coordinate system is referred to in the following figures. Particularly, the x-axis refers to an axis tangent to the circle of rotation of gantry 12. The y-axis refers to a radial axis extending from the iso center (ISO) of gantry 12 toward the x-ray tube focal spot. The z-axis is a longitudinal axis (in/out) with respect tot he scan plan. The patient is translated along the z-axis on patient table 20 during scanning.

Figure 7:
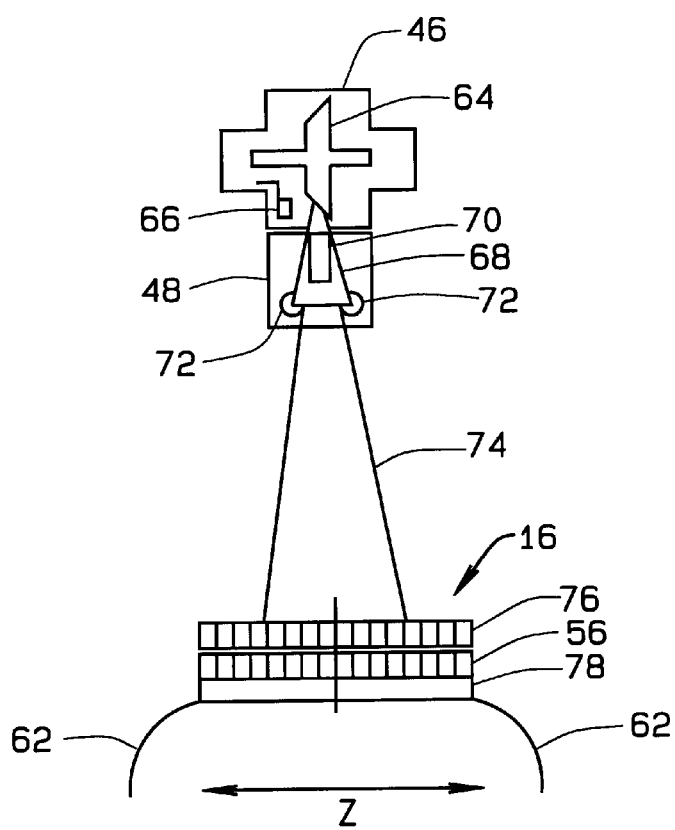
FIG. 7 is a schematic illustration of x-ray generation and detector components viewed from a side of the gantry.

Referring now to FIG. 7, and in multislice scanning, data is collected at various z-axis locations. Particularly, FIG. 7 is a schematic illustration of system 10 viewed from a side of the gantry 12. X-ray tube 46 includes an anode/target 64 and a cathode 66. An uncollimated x-ray beam 68 is emitted by tube 46 and passes through cam collimator 48. Collimator 48 includes a bowtie filter 70 and tungsten cams 72. Additional details regarding filter 70 are set forth in copending U.S. patent application Ser. No. (15-CT-4762), which is assigned to the present assignee and hereby incorporated herein, in its entirety, by reference.

As explained in connection with FIG. 2, the position of cams 72 is controlled by an on-board controller 40 which receives its commands from host computer 24, as prescribed by the operator using the user interface, via SRU 32 and stationary controller 34. Stepper motors, for example, are connected to cams 72 for precisely controlling the position of cams 72. Cams 72 of cam collimator 48 can be independently adjusted with respect to the spacing between cams 72 and their location relative to the center of the collimator opening depending on the user selected data collection mode.

A collimated x-ray beam 74 is emitted from cam collimator 48, and beam 74 passes through patient 18 (FIG. 1) and impinges upon detector 16. As described above, detector 16 includes a collimator 76, a scintillator array 56, and a photodiode/switching array 78 (the photodiode and switching arrays are shown as one unit in FIG. 7 but may be separate arrays as described above). Outputs from array 78 are supplied, via a flex cable, to SDAS 42 for processing.

The following description relates to operation of cam collimator 48 and detector 16 for providing scalability in the number of slices and the slice thickness. Although the operation of cam collimator 48 and the operation of detector 16 are sometimes described separately herein, it should be understood that collimator 48 and detector 16 operate in combination to provide the desired number of slices and slice thickness.

Figure 8:
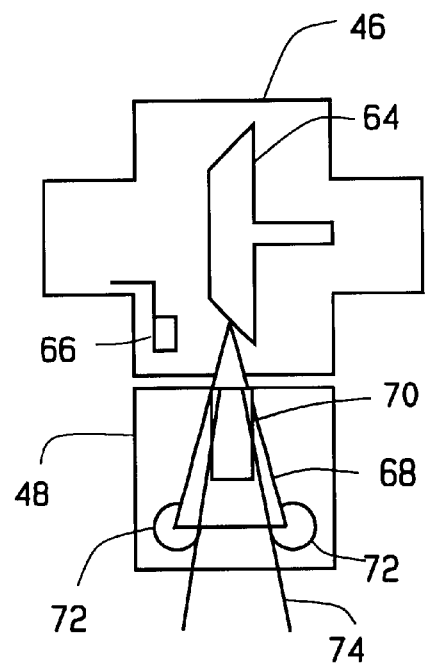
FIGS. 8 and 9 illustrate operation of the cam collimator in the CT system illustrated in FIG. 1.
Figure 9:
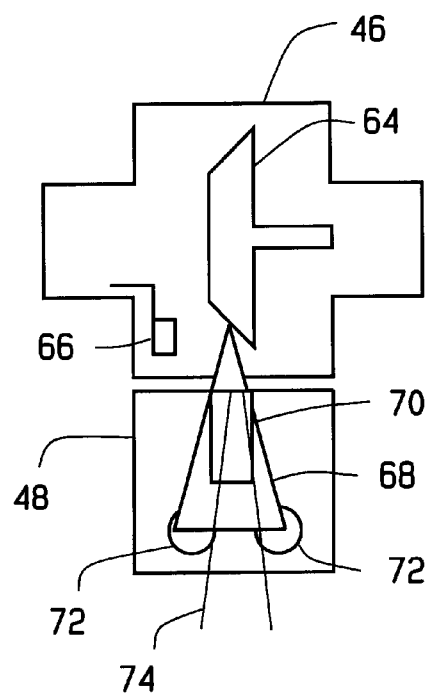

More specifically, FIGS. 8 and 9 illustrate operation of cam collimator 48. FIG. 8 illustrates cam collimator 48 configured to emit a centered wide beam (e.g., a beam for obtaining 4 slices of data with a 5 mm slice thickness). For a narrow centered beam, and as shown in FIG. 9, cams 72 are moved inward an equal amount relative to a center of beam 68. For example, the cam collimator configured shown in FIG. 9 could be used for obtaining 4 slices of data with a 1.25 mm slice thickness.

As described below in more detail, by controlling the position and width of beam 74 at cam collimator 48, scans can be performed to obtain data for many different slice numbers and slice thicknesses. For example, FIG. 10 corresponds to a selected detector configuration when it is desired to obtain 4 slices of data with a slice thickness of 5.0 mm. Cams 72 are separated wide apart in the z-axis direction to provide 20 mm collimation, and the photodiode outputs are combined by switching array 78 into four separate slices. Particularly, each slice of data combines the outputs of four photodiodes into one signal (1A, 2A, 1B, and 2B), and each slice data signal (1A, 2A, 1B, and 2B) is supplied to SDAS 42 via flex cables 62.

Figure 10:
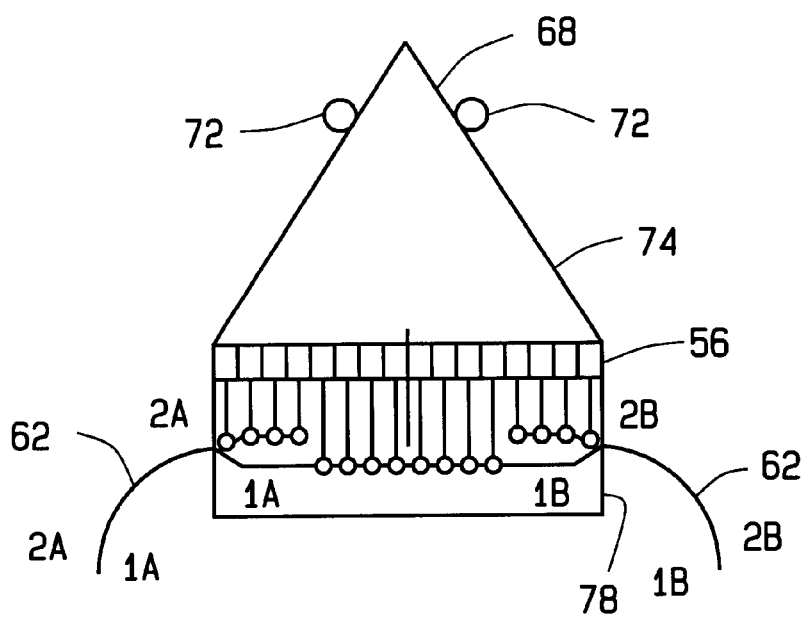
FIGS. 10, 11, and 12 schematically illustrate collection of scan data for various number of slices and slice thicknesses.
Figure 11:
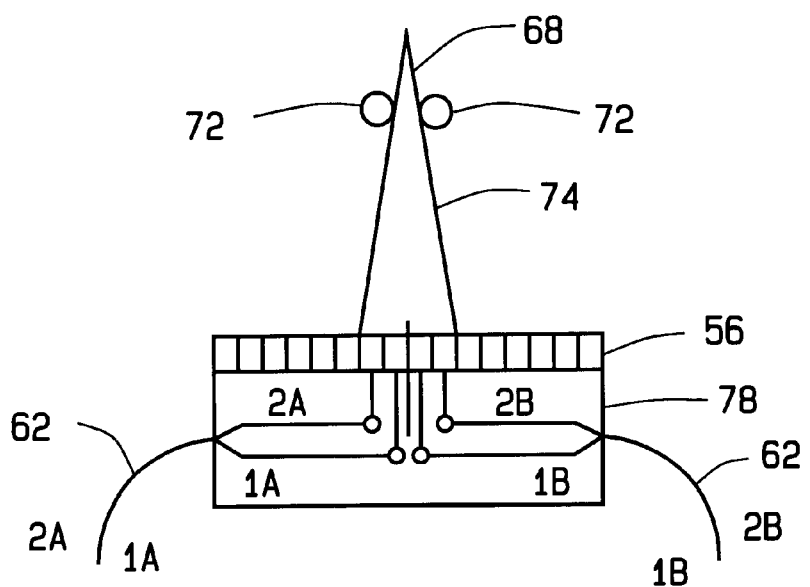

For four slices of data with a 1.25 mm slice thickness, the detector configuration shown in FIG. 11 may be utilized, Particularly, cams 72 are not separated as wide apart as for the 5.0 mm slice thickness (FIG. 10). Rather, cams 72 are separated in the z-axis direction to provide 5 mm collimation, and the photodiode outputs are combined by switching array 78 into four separate slices. Particularly, each slice of data combines the outputs of one photodiodes into one signal (1A, 2A, 1B, and 2B), and each slice data signal (1A, 2A, 1B, and 2B) is supplied to SDAS 42 via flex cables 62.

Figure 12:
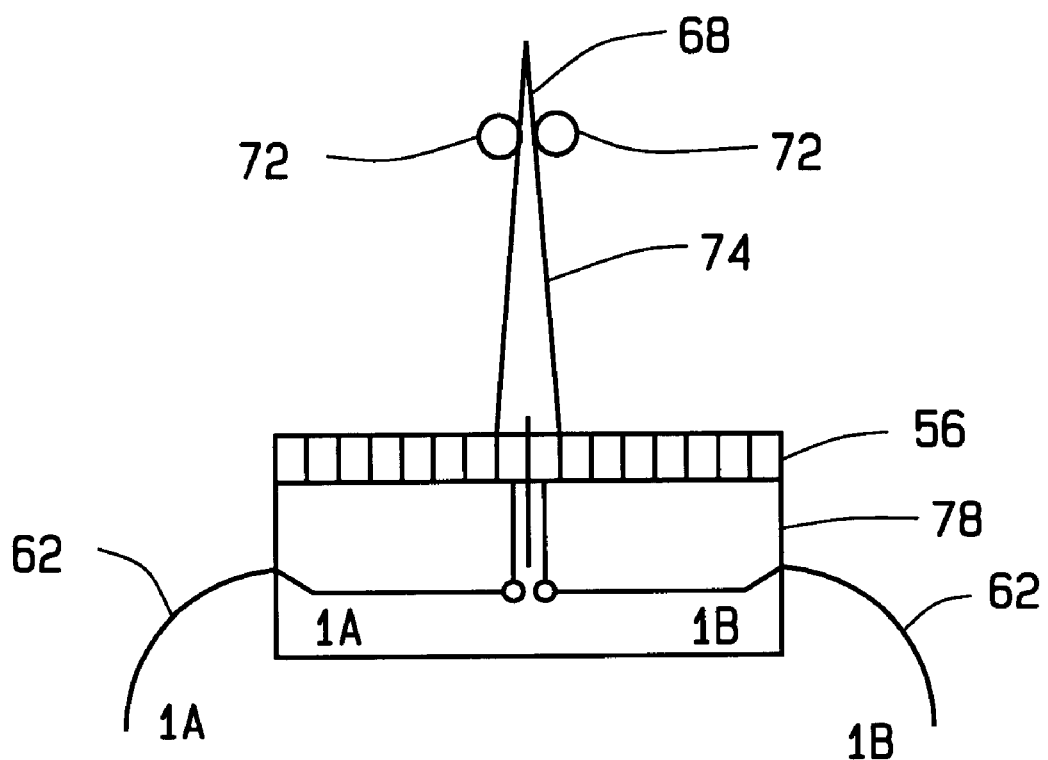

Of course, many other combinations of slice number and slice thickness are possible using system 10. For example, and referring to FIG. 12, for two slices of data with a 1.25 mm slice thickness, cams 72 are separated in the z-axis direction to provide 2.5 mm collimation. The photodiode outputs are combined by switching array 78 into two separate slices. Particularly, each slice of data combines the outputs of one photodiode into one signal (1A and 1B), and each slice data signal (1A and 1B) is supplied to SDAS 42 via flex cables 62. By controlling cam collimator 48 and channel summation along the z-axis as described above, scan data can be collected for many different slice numbers and slice thicknesses.

Many variations and additions to the above described exemplary system can be made. For example, a graphic based user interface which enables the user to easily prescribe multislice scan and image reconstruction in various forms with, for example, optimum table speed, x-ray beam collimation, data collection slice thickness, x-ray beam voltage and current values, as well as the reconstruction method to obtain the desired image quality. Such an interface may be activated by a touch screen, voice, or other known interface methodologies that are easy to use and understand. The host computer can be preprogrammed to include various default modes based upon the type of scan being performed to further simplify the operator performed selections.

The above described scalable multislice system can be easily and simply operated to collect one, two, or more slices of data. Such system also provides the operator with prospective and retrospective image thickness options for the selected scan parameters.

While the invention has been described in terms of various specific embodiments, those skilled in the art will recognize that the invention can be practiced with modification within the spirit and scope of the claims.

What is claimed is:

1. An imaging system comprising:
    a detector comprising multiple detector cells extending along a z-axis and configured to collect multiple slices of data;
    a scalable data acquisition system coupled to said detector and configured to convert signals received from said detector to digital form; and
    a host computer comprising a user interface for enabling a user to select scan parameters, said user interface comprising selectable scan parameters of helical, cine, and axial scan for multiple slice scans and said scan parameters comprising prospective and retrospective slice thicknesses, wherein said prospective slice thicknesses are displayed in a first color and said retrospective slice thicknesses are displayed in a second color.

2. A system in accordance with claim 1 wherein said scan parameters for the helical scan comprises a pitch speed.

3. A system in accordance with claim 2 wherein said imaging system further comprises a table for supporting a patient, and wherein said scan parameters for the helical scan further comprises a table speed.

4. A system in accordance with claim 1 wherein user interface adjusts said collimator based on said selectable scan parameters for helical and axial scans.

5. A system in accordance with claim 1 wherein said detector comprises a plurality of modules.

6. A system in accordance with claim 5 wherein at least one of said modules comprises a scintillator array and a photodiode array, said scintillator array positioned over and optically coupled to said photodiode array.

7. A system in accordance with claim 6 wherein signals output by photodiodes of said photodiode array are selectively combinable based on at least one of a selected slice thickness and number of slices.

8. A computed tomography system comprising a host computer comprising a user interface, said host computer programmed to enable an operator to prescribe scan parameters for helical, cine, and axial scans, said scan parameters comprising at least data collection slice thickness and number of slices, wherein said scan parameters for the helical, axial and cine scans comprises prospective and retrospective slice thicknesses, wherein said prospective slice thicknesses are displayed in a first color and said retrospective slice thicknesses are displayed in a second color.

9. A system in accordance with claim 8 wherein said scan parameters for the helical scan comprises a pitch speed.

10. A system in accordance with claim 9 wherein said imaging system further comprises a table for supporting a patient, and wherein said scan parameters for the helical scan further comprises a table speed.

11. A system in accordance with claim 8 wherein said system further comprises a prepatient collimator coupled to said host computer, said prepatient collimator comprises a cam collimator comprising at least one adjustable cam, and wherein said host computer is further programmed to adjust said collimator based on said selectable scan parameters for helical and axial scans.

12. A method of enabling an operator to prescribe scan parameters for an imaging system, the imaging system including a host computer having a user interface, said method comprising the steps of:
    allowing the operator to select a mode of operation;
    displaying available scan parameters for the selected mode of operation; and
    displaying prospective and retrospective image thicknesses available for the selected scan mode using a different color.

13. A method in accordance with claim 12 wherein the system further includes a prepatient collimator coupled to the host computer, the prepatient collimator includes a cam collimator having at least one adjustable cam, and wherein said method further comprises the step of adjusting the collimator based on the selected scan mode.

14. A method in accordance with claim 12 wherein allowing the operator to select a scan mode of operation comprises the step of selecting one of a helical mode, axial mode and a cine mode.

15. A method in accordance with claim 14 wherein allowing the operator to select a mode of operation further comprises the step of selecting scan parameters for each scan mode.

16. A method in accordance with claim 15 wherein the imaging system includes a movable table for supporting a patient, and wherein selecting scan parameters for the helical scan mode comprises the step of selecting a table speed.

17. A method in accordance with claim 16 wherein selecting scan parameters for the helical scan mode further comprises the step of selecting a pitch speed.

* * * * *